Figure 1:
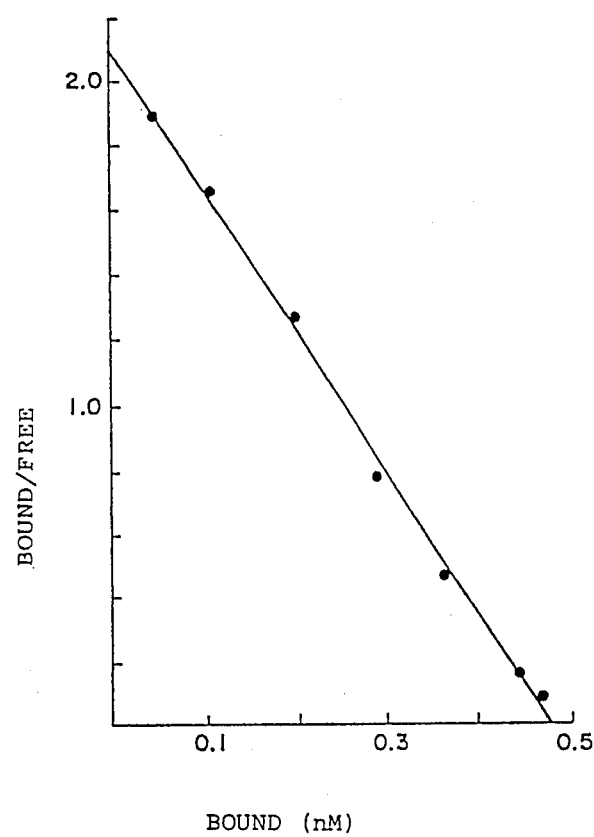

United States Patent [19]

Kubodera et al.

[11] Patent Number: 4,740,476
[45] Date of Patent: Apr. 26, 1988

[54] IMMUNOASSAY FOR ESTRIOL-3-SULFATE

[75] Inventors: Akiko Kubodera, Matsudo; Touichi Tanaka, Tokyo, both of Japan

[73] Assignee: Nihon Medi-Physics Co., Ltd., Hyogo, Japan

[21] Appl. No.: 789,977

[22] Filed: Oct. 21, 1985

[30] Foreign Application Priority Data

Oct. 19, 1984 [JP] Japan .................. 59-218275
Nov. 30, 1984 [JP] Japan .................. 59-254591

[51] Int. Cl.⁴ .............. G01N 33/531; G01N 33/537; G01N 33/543; G01N 33/548
[52] U.S. Cl. .................. 436/518; 436/529; 436/538; 436/543; 436/547; 436/808; 436/817; 436/822; 436/825; 436/826; 530/403; 530/404; 530/405; 530/406; 530/807
[58] Field of Search ............. 530/403, 404, 405, 406, 530/807; 436/518, 536, 543, 547, 808, 817, 822, 825, 826, 529, 538

[56] References Cited

PUBLICATIONS

B. F. Erlanger, *Meth. Enzmology*, vol. 70, 85–104, 1980.
T. Nambara et al, *J. Steroid Biochem.*, 21, 199–203, 1984.
T. Tanaka et al, *Steroids*, 43, 235–242, 1984.
T. Tanaka et al, *Steroids*, 46, 649–657, 1985.
T. Tanaka et al, *J. Steroid Biochem.*, 22, 285–288, 1985.

Primary Examiner—Sidney Marantz
Assistant Examiner—David A. Saunders

[57] ABSTRACT

A process for producing an antibody having a specificity to estriol-3-sulfate, which comprises administering a 6-substituted-estriol-3-sulfate protein conjugate of the formula:

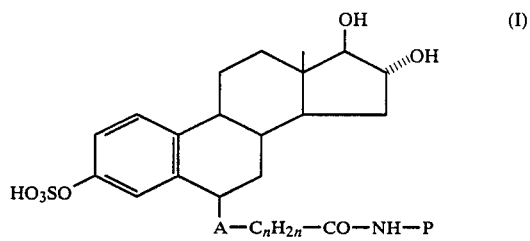

wherein A is =N—O— or —O—CO—, n is an integer of 1 to 4 and —NH—P is the residue of a protein excluding a hydrogen atom in the amino form therefrom parenterally to a living body of a vertebrate animal so as to produce the antibody in the living body and collecting a body fluid comprising the antibody from the living body.

19 Claims, 4 Drawing Sheets

IMMUNOASSAY FOR ESTRIOL-3-SULFATE

The present invention realates to an immunoassay for estriol-3-sulfate. More particularly, it relates to 6-substituted-estriol-3-sulfates, which are useful as reagents for preparation of an antibody having a specificity to estriol-3-sulfate, and their production and use.

Estriol-3-sulfate is reported to be a major metabolite of estriol in the fetus (U. Goebelsmann et al.: Acta Endocrinol., 50, 273 (1965) and 52, 550 (1966)). It is also suggested that estriol-3-sulfate may be transferred unchanged from the fetal to the maternal compartment. In the diagnosis of the placenta in the process of pregnancy or of the functional growth of the fetus, measurement of estriol-3-sulfate has thus a great significance. However, measurement of estriol-3-sulfate by conventional procedures requires troublesome operations such as hydrolysis, solvolysis, extraction with solvents, separation by chromatography, etc., and no reliable method for direct assay of estriol-3-sulfate has been developed yet.

In recent years, much attention has been directed to immunoassay in various fields including clinical chemistry, because it is highly sensitive. Aiming at establishment of a reliable assay method for quantitative determination of estriol-3-sulfate, an extensive study has been made, and an antibody showing a high specificity to estriol-3-sulfate has now been successfully produced. The combined use of such antibody with labeled estriol-3-sulfate can accomplish the immunoassay of estriol-3-sulfate by a simple operation with a high sensitivity without necessitating any troublesome operation such as hydrolysis, solvolysis, extraction with solvents and separation by chromatography.

In the present invention, the characteristic feature resides in the use of a 6-substituted-estriol-3-sulfate protein conjugate of the formula:

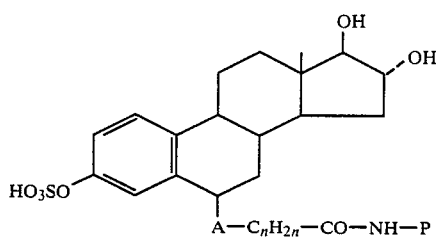

(I)

wherein A is $=N-O-$ or $-O-CO-$, n is an integer of 1 to 4 and $-NH-P$ is the residue of a protein excluding a hydrogen atom in the amino form therefrom (hereinafter referred to as "ESP conjugate") for production of an antibody specific to estriol-3-sulfate.

The ESP conjugate (I) is a novel substance and can be produced by condensing the corresponding carboxylic acid of the formula:

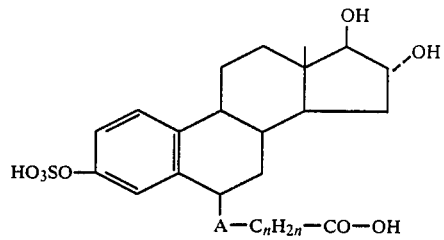

wherein A and n are each as defined above with a protein of the formula:

$$H_2N-P$$

wherein P is as defined above in the presence of a condensing agent such as a water-soluble carbodiimide in an aqueous medium. More specifically, the ESP conjugate (I) can be prepared from 6-oxoestriol-3,16,17-triacylate by the procedure as shown in the following scheme when, for instance, A is $=N-O-$, n is an integer of 1 and $-NH-P$ is the residue of a bovine serum albumin excluding a hydrogen atom in the amino form therefrom:

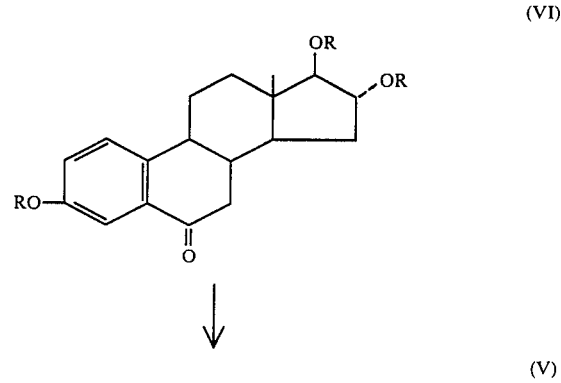

(VI)

(V)

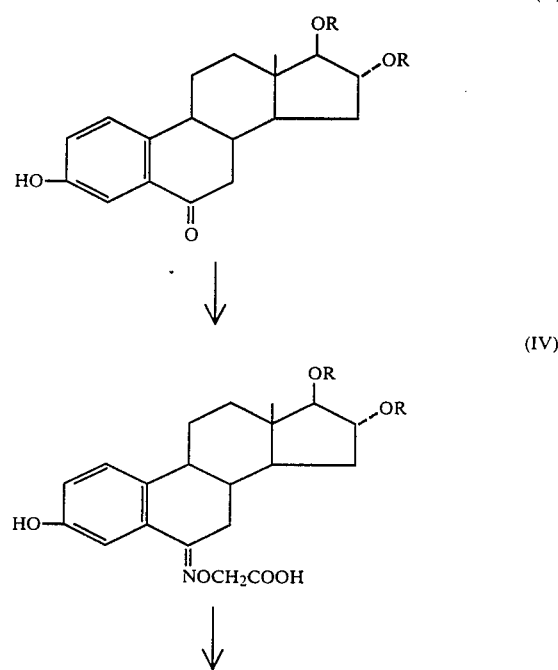

(IV)

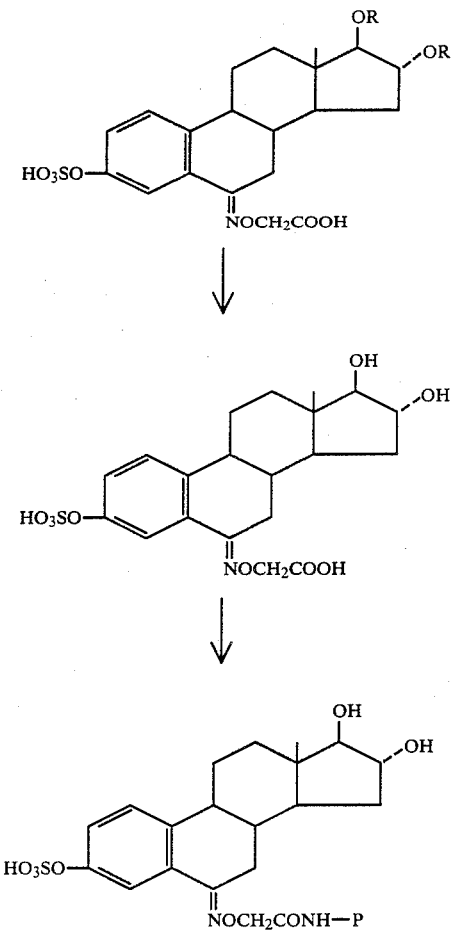

wherein R is an acyl group such as lower alkanol (e.g. acetyl, propionyl, butyryl) or benzoyl.

In the above procedure, the 6-oxoestriol-3,16,17-triacylate (VI) is first subjected to partial hydrolysis to give the 6-oxoestriol-16,17-diacylate (V). The partial hydrolysis may be accomplished, for instance, by treatment with a base such as an inorganic base, particularly alkali carbonate (e.g. sodium carbonate, potassium carbonate) or alkali bicarbonate (e.g. sodium bicarbonate, potassium bicarbonate) in an aqueous medium at a temperature of −10° to 30° C. The aqueous medium may contain any inert water-miscible organic solvent such as an alkanol (e.g. methanol, ethanol).

The resulting diacylate (V) is then condensed with O-carboxymethylhydroxylamine to give the 6-oxoestriol-O-carboxymethyloxime-16,17-diacylate (IV). The condensation may be carried out by treatment of the diacylate (V) with O-carboxymethylhydroxylamine in an inert solvent (e.g. methanol, ethanol) at a temperature of −10° to 30° C.

The resulting oxime derivative (IV) is then reacted with chlorosulfonic acid in the presence of a base such as an organic base (e.g. pyridine, triethylamine, dimethylaniline) at a temperature of room temperature (0° to 30° C.) to the reflux temperature to give the 6-oxoestriol-3-sulfate-O-carboxymethyloxime-16,17-diacylate (III). When desired, any inert solvent (e.g. benzene, toluene) may be used.

The thus prepared 3-sulfate-O-carboxymethyloxime 16,17-diacylate (III) is subjected to hydrolysis to give the corresponding 3-sulfate-O-carboxymethyloxime (II), i.e. 6-oxoestriol-3-sulfate-O-carboxymethyloxime. The hydrolysis may be accomplished by a per se conventional procedure, for instance, treatment with a base such as an inorganic base (e.g. sodium hydroxide, potassium hydroxide) in an aqueous medium at room temperature (0° to 30° C.).

The thus obtained 3-sulfate-O-carboxymethyloxime (II) is condensed with a protein such as bovine serum albumin in the presence of a condensing agent such as a water-soluble carbodiimide (e.g. 1-ethyl-3-(3-dimethylaminopropyl)carbodiimide) to give the ESP conjugate (Ia). The condensation is preferably effected under a mild conditions, for instance, at a temperature of 0° to 10° C. with gentle stirring. When desired, any inert solvent (e.g. pyridine, phosphate buffer) may be used.

When, for instance, A is —OCO—, n is an integer of 2 and —NH—P is the residue of a bovine serum albumin excluding a hydrogen atom in the amino form, the ESP conjugate (Ib) can be produced by reducing the 6-oxoestriol-3,16,17-triacylate (VI) by a conventional procedure for conversion of a carbonyl group into a hydroxymethylene group to give the 6-hydroxyestriol-3,16,17-triacylate, which is then reacted with succinic anhydride to give the corresponding hemisuccinate at the 6-position. The hemisuccinate is then subjected to hydrolysis with a base such as potassium carbonate in an aqueous medium whereby the acyl group at the 3-position is selectively eliminated. The resultant 6-hydroxyestriol-16,17-diacylate-6-hemisuccinate is then subjected to sulfation at the 3-position, hydrolysis at the 16 and 17-positions and amidation at the 6-side chain in this order in the same manner as above so that the ESP conjugate (Ib) can be obtained.

As the protein which is represented by the formula: P—NH$_2$, there may be used any one which is conventionally employed as a carrier for a hapten in the field of immunochemistry, and its specific examples are albumin, globulin, etc. Particularly, the use of bovine serum albumin, rabbit serum albumin, etc. is favorable.

For production of the antibody to estriol-3-sulfate by the use of the ESP conjugate, the ESP conjugate is administered parenterally to a living body chosen from a vertebrate animal (e.g. cattle, horse, sheep, goat, rabbit, rat, mouse) to produce an antibody in the living body. Then, a humor or body fluid (e.g. blood) is taken from the living body, optionally followed by removal of impurities. Usually, a serum containing an antibody, i.e. an anti-serum, is employed.

As the labeled antigen to be used in combination with the antibody, there may be used estriol-3-sulfate as appropriately labeled. For labeling, a radioactive substance, an enzyme, a fluorescent substance, a luminescent substance, etc. are usable. These labeling substances may be introduced into any appropriate position of estriol-3-sulfate as long as the immune activity of the labeled antigen is retained. When, for instance, labeling is effected with $^3$H or $^{14}$C, the element constituting estriol-3-sulfate is substituted with the same, and therefore the immune activity of the labeled antigen is not changed from that of estriol-3-sulfate itself. When labeling is effected with $^{125}$I or $^{131}$I, it is introduced into estriol-3-sulfate with intervention of an appropriate coupling agent so that its affinity to an antibody is somewhat different from that of estriol 3-sulfate, and therefore care must be taken for the maintenance of the immune activity.

Labeling may be accomplished by any per se conventional procedure. For instance, labeling with radioactive iodine may be effected by the direct method such as a method using an oxidizing agent (e.g. chloramin T, iodine chloride) or a method using an enzyme (e.g. lactoperoxidase), or by the indirect method which comprises introduction of a functional group (e.g. carboxyl, amino, thiol) into estriol-3-sulfate and combination of the functional group with an iodinated compound (e.g. iodinated tyramine, iodinated tyrosine, iodinated histamine, Bolton-Hunter reagent) labeled with a radioactive isotope. A typical example of the labeling procedure with radioactive iodine comprises condensing 6-oxoestriol-3-sulfate O-carboxymethyloxime with iodinated histamine labeled with a radioactive iodine atom in the presence of a water-soluble carbodiimide to obtain the objective radioactive iodine-labeled antigen. In place of the iodinated histamine, there may be used beta-(4-hydroxyphenyl)ethyl-amine or beta-(4-hydroxyphenyl)alanine methyl ester labeled with a radioactive iodine atom on the benzene ring.

Application of the immunoassay of the invention to a serum sample (containing an unknown amount of estriol-3-sulfate) obtained from a human being to be diagnosed may be carried out in the following manner. Namely, various amounts of estriol 3-sulfate are added to sera to make standard solutions. To each of the standard solutions, a designed amount of the labeled antigen as above mentioned is added, and the antibody as above mentioned is added thereto so as to effect the antigen-antibody reaction under a per se conventional operation condition. The antigen-antibody combined product (B) and the antigen fraction (F) with which the antibody is not combined are separated by a per se conventional separation procedure such as electrophoresis, gel filtration, salting out or adsorption. The labeling potency of either one of (B) and (F) is measured by an appropriate assay method depending on the labeling procedure as adopted on the production of the labeled antigen, and the further operation proceeds as above. Ultimately, the estriol-3-sulfate level in the serum sample is determined with reference to the calibration curve. In the above antigen-antibody reaction, the presence of glutamine is preferred in order to enhance the accuracy of the immunoassay.

Practical and presently preferred embodiments of the invention are illustratively shown in the following Examples. Free steroids, bovine serum albumin (BSA) and bovine gamma-globulin (BGG) as used in those Examples are the commercial products manufactured by Sigma Chemical Co., Ltd., and the other reagents are those manufactured by Nakarai Chemical Co., Ltd.

EXAMPLE 1

(A) Preparation of 6-oxoestriol-16,17-diacetate (V: R=COCH$_3$):

To a solution of 6-oxoestriol-3,16,17-triacetate (VI: R=COCH$_3$) (Wright et al.: Steroids, 21, 755 (1973)) (500 mg) in methanol (30 ml), 5% potassium carbonate solution (5 ml) was added, and the resultant solution was allowed to stand while cooling with ice for 2 hours. The reaction mixture was neutralized with 0.1N hydrochloric acid, concentrated and extracted with ethyl acetate. The extract was washed with water, dried over anhydrous sodium sulfate and concentrated under reduced pressure. The residue was chromatographed on silica gel and eluted with a mixture of n-hexane and ethyl acetate (2:1). The eluate was recrystallized from methanol to give 6-oxoestriol-16,17-diacetate (V: R=COCH$_3$) (248 mg) as colorless prisms. M.P., 236° to 239° C.

IR (KBr): $\nu_{max}$3420 (Ar—OH), 1740 (—OCOCH$_3$), 1760 (CO). NMR (CDCl$_3$): δ 0.84 (3H, s, 18—CH$_3$), 2.06 (3H, s, 17—OCOCH$_3$), 2.09 (3H, s, 16—OCOCH$_3$), 4.92 (1H, d, J=6 Hz, 17—H), 6.98-7.54 (3H, m, Ar—H).

(B) Preparation of 6-oxoestriol-O-carboxymethyloxime-16,17-diacetate (IV: R=COCH$_3$):

To a solution of 6-oxoestriol-16,17-diacetate (V: R=COCH$_3$) (150 mg) as obtained in (A) in methanol (10 ml), O-carboxymethylhydroxylamine hydrochloride (100 mg) was added. The resultant solution was neutralized with 1N NaOH solution and allowed to stand at room temperature overnight. The resulting solution was concentrated and extracted with ethyl acetate. The extract was chromatographed on silica gel and eluted with a mixture of n-hexane and ethyl acetate (2:1). The eluate was recrystallized from methanol to give 6-oxoestriol-O-carboxymethyloxime-16,17-diacetate (IV: R=COCH$_3$) (126 mg) as colorless prisms. M.P., 188° to 190° C.

IR (KBr): $\nu_{max}$3400 (Ar—OH), 1620-1540 (C=N—, COOH). NMR (CDCl$_3$): δ 0.76 (3H, s, 18—CH$_3$), 2.05 (3H, s, 17—OCOCH$_3$), 2.08 (3H, s, 16—OCOCH$_3$), 4.72 (2H, s, =NOCH$_2$), 6.82-7.37 (3H, m, Ar—H).

Anal. Calcd. for C$_{24}$H$_{29}$O$_8$N: C, 62.73; H, 6.36; N, 3.50. Found: C, 63.75; H, 7.18; N, 2.30.

(C) Preparation of 6-oxoestriol-3-sulfate-O-carboxymethyloxime-16,17-diacetate (III: R=COCH$_3$):

A solution of chlorosulfonic acid (200 mg) in pyridine (4 ml) cooled at −10° C. was added to a solution of 6-oxoestriol-O-carboxymethyloxime-16,17-diacetate (100 mg) as obtained in (B) in pyridine (1.5 ml), and the resultant mixture was stirred at 37° C. for 2.5 hours, whereby 6-oxoestriol-3-sulfate-O-carboxymethyloxime-16,17-diacetate (III: R=COCH$_3$) was produced.

(D) Preparation of 6-oxoestriol-3-sulfate-O-carboxymethyloxime (II):

The reaction mixture containing 6-oxoestriol-3-sulfate-O-carboxymethyloxime-16,17-diacetate (III: R=COCH$_3$) as obtained in (C) was poured into 0.1N NaOH solution and allowed to stand at room temperature overnight. The resultant solution was diluted with water (300 ml) and passed through a column of Amberlite XAD-2, followed by washing with water. The column was eluted with methanol (50 ml). The eluate was concentrated at 25° C. under reduced pressure. The residue was subjected to thin layer chromatography using a mixture of chloroform, methanol and ammonia (15:5:1 by volume). The fraction corresponding to Rf=0.1 was eluted with a mixture of chloroform, methanol and ammonia (15:7:1 by volume) to give 6-oxoestriol-3-sulfate-O-carboxymethyloxime (II) (78 mg) as a colorless amorphous substance. M.P., higher than 300° C.

IR (KBr): $\nu_{max}$1060 (—SO$_3$H). NMR (CD$_3$OD): δ 0.76 (3H, s, 18—CH$_3$), 4.52 (2H, s, =NOCH$_2$), 7.27 (2H, s, 1— and 2—H), 7.76 (1H, s, 4—H).

Anal. Cacld. for C$_{20}$H$_{23}$O$_9$NS.Na$_2$.2H$_2$O: C, 44.87; H, 5.08; N, 2.62. Found: C, 45.19; H, 4.96; N, 2.65.

(E) Preparation of 6-oxoestriol-3-sulfate-O-carboxymethyloxime-BSA conjugate (Ia: P=bovine serum albumin (BSA)):

A solution of 1-ethyl-3-(3-dimethylaminopropyl)carbodiimide hydrochloride (100 mg) and bovine serum albumin (50 mg) in 0.1M phosphate buffer (pH, 7.1) (0.5 ml) was added dropwise to a solution of 6-oxoestriol-3-sulfate-O-carboxymethyloxime (II) (30 mg) as obtained in (D) in pyridine (0.5 ml), and the resultant mixture was stirred at 4° C. overnight. The produced solution was dialyzed and lyophilized to give 6-oxoestriol-3-sulfate-O-carboxymethyloxime-BSA conjugate (Ia: P=BSA) (47 mg).

The above hapten-BSA conjugate (Ia) (6-oxoestriol-3-sulfate-O-carboxymethyloxime-BSA conjugate) was confirmed to have about 14 steroid molecules in one molecule by coloring reaction with conc. sulfuric acid.

EXAMPLE 2

Preparation of the antibody of estriol-3-sulfate:

Three male guinea pigs were used for immunization. 6-Oxoestriol-3-sulfate-O-carboxymethyloxime-BSA conjugate (Ia) (0.5 mg) was dissolved in a sterilized isotonic saline solution (0.25 ml) and emulsified with Freund's complete adjuvant (0.25 ml). The emulsion was subcutaneously injected into each thigh and below each shoulder blade. Subcutaneous injections were repeated 14 and 28 days after the initial injection and every 30 days thereafter. The animals were bled 10 days after the fourth booster injection. The sera were separated by centrifugation at 3500 r.p.m. for 20 minutes and stored at −25° C.

EXAMPLE 3

Preparation of the immobilized antibody:

The antibody was coupled to CNBr-activated Sepharose-4B (manufactured by Pharmacia Fine Chemical Co., Ltd.) by the method of Hervey et al (Cancer Res. 35, 3001–3008 (1975)). Anti-esterol-3-sulfate antiserum was mixed with ammonium sulfate (500 g/liter) and allowed to stand at room temperature for 10 minutes, followed by centrifugation at 2500 rpm for 20 minutes. The precipitate was dissolved in distilled water (1.0 ml) and dialyzed against borate buffer (0.05 mol/liter; pH, 8.0). The solution provided the crude "globulin" fraction. CNBr-Activated Sepharose-4B (200 mg) was washed away with hydrochloric acid ($10^{-3}$ mol/liter) (100 ml). The antiserum (1.0 ml) treated with ammonium sulfate (500 g/liter) was diluted with $NaHCO_3$ buffer (0.1 mol/liter; pH, 8.0) (5.0 ml) (containing NaCl (0.5 mol/liter)), mixed with the gel, and the mixture was stirred at 4° C. overnight. Unbound material was washed away with a coupling buffer, and remaining active groups were reacted with ethanolamine (1 mol/liter; pH, 8.0) for 1 hour. Three washing cycle was used to remove nocovalently adsorbed protein, each cycle consisting of a wash at acetate buffer (0.1 mol/liter; pH, 4.0) (5.0 ml) (containing NaCl (1.0 mol/liter)), followed by a wash at borate buffer (0.1 mol/liter; pH, 8.0) (containing NaCl (1.0 mol/liter)). The immobilized antibody was highly stable at 4° C., and no substantial change in binding affinity was revealed over a period of several months.

EXAMPLE 4

Preparation of [6,7-$^3$H]-estriol-3-sulfate as the labeled antigen:

The enzyme preparation was obtained from a guinea pig liver (M. Bouthillier et al.: Steroids, 38, 523 (1981)). The liver homogenate was treated with Norit-A in order to remove endogeous steroids. [6,7-$^3$H]-esteriol (100 uCi) was incubated with adenosine 3'-phosphate 5'-phosphosulfate (1 ug) and the liver homogenate (200 ul) in 0.05M tris-HCl buffer (pH, 7.4) (containing 0.001M $MgCl_2$, 0.025M cysteine and 0.001M dithiothreitol) at 37° C. for 2 hours. The reaction mixture was deproteinized with ethanol and centrifuged at 1800 rpm for 15 minutes. The supernatant was diluted with 0.05M phosphate buffer (pH, 7.5) (30 ml) was passed through an Amberlite XAD-2 column (0.5×10 cm). The sulfate fraction was eluted with methanol, evaporated under nitrogen stream and purified by preparative thin layer chromatography using a mixture of chloroform, methanol and ammonia (15:5:1 by volume). The band (Rf=0.32) corresponding to authentic sample was eluted with a mixture of methanol and ammonia (95:1 by volume). The eluate was further purified by column (0.5×15 cm) chromatography on Sephadex LH-20 using methanol as an eluant, and the desired fraction was collected and concentrated in vacuo to give [6,7-$^3$H]-estriol-3-sulfate (45.3 Ci/mmol) (10.9 uCi) in 13.6% yield. Radiochemical purity was greater than 98% by thin layer chromatography on silica gel G.

EXAMPLE 5

Measurement of estriol-3-sulfate:

[$^3$H]-Estriol-3-sulfate (5500 dpm) in 0.05 mol/liter phosphate buffer (pH, 7.5; 0.1 ml) was added to a homogeneous suspension of immobilized antibody (1:500 by volume) (0.2 ml) diluted with phosphate buffer (0.05 mol/liter; pH, 7.5) and allowed to stand at room temperature for 15 minutes. A plasma specimen (0.1 ml) diluted with tris-HCl buffer (0.1 mol/liter; pH, 8.3) (containing glutamine (0.1 mol/liter)) was added thereto, and the resulting solution was incubated at 4° C. for 16 hours. The mixture was centrifuged at 3500 rpm for 20 minutes. A 0.2 ml aliquot of each supernatant was taken into a counting vial and admixed with Bray's scintillator, and radioactivity was counted in an Aloka LSC-673 liquid scintillation spectrometer. The Scatchard plot of the obtained results indicated such a high affinity to estriol-3-sulfate as an association constant (Ka) of $4.3 \times 10^9$ liter/mol (cf. FIG. 1 of the accompanying drawing showing the Scatchard plot graph of anti-estriol-3-sulfate antibody immobilized on Sepharose 4B).

EXAMPLE 6

Figure 2:
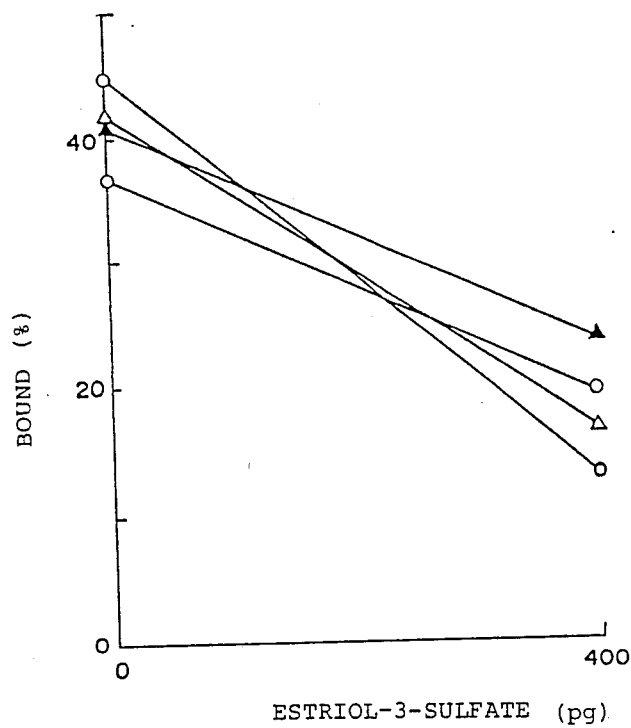

Investigation on the diluted aliquot of a plasma specimen:

In order to reduce the non-specific binding of estriol-3-sulfate to plasma, a certain substance dissolved in a buffer was added to an antigen-antibody mixture containing a plasma specimen, and then investigation was made thereon. Namely, glutamine, cysteine or glycine was added to a plasma specimen diluted with tris-hydrochloric acid buffer (0.1 mol/liter) as given in Example 5, and measurement of estriol-3-sulfate was carried out in the same manner as in Example 5. The results are indicated in FIG. 2 of the accompanying drawing, which shows the effect of various substances on the non-specific binding of estriol-3-sulfate to a plasma protein and where O—O is the case in which no substance added, ▲ — ▲ is the case in which cysteine (0.1 mol/liter) added, △—△ is the case in which glycine (0.2 mol/liter) added and ● — ● is the case in which glutamine (0.1 mol/liter) added.

EXAMPLE 7

Cross-reaction of various steroids:

Specificity

The specificity is evaluated as cross reaction of other steroids against immobilized antibody. The cross-reactivity is determined by calculating the mass ratio of non-labeled estriol-3-sulfate to each steriod required to show 50% inhibition of the labeled estiol-3-sulfate binding to the antibody. The results are shown in Table 1.

TABLE 1

Percent cross-reactivities of various steroids with anti-estriol-3-sulfate antibody immobilized on Sepharose 4B

| Steroid | Cross-reaction (%) |
| --- | --- |
| Estriol-3-sulfate | 100 |
| Estrone sulfate | 0.060 |
| Estradiol-3-sulfate | 0.144 |
| Dehydroepiandrosterone sulfate | 0.077 |
| Cholesterol sulfate | 0.081 |
| Testosterone sulfate | 0.004 |
| Estrone glucuronide | <0.001 |
| Estriol-3-glucuronide | 0.050 |
| Estradiol-17-glucuronide | <0.001 |
| Estriol-16-glucuronide | <0.001 |
| Estriol-17-glucuronide | <0.001 |
| Estrone methyl ether | <0.001 |
| Estrone-3-methyl ether | <0.001 |
| 2-Hydroxyestrone | <0.001 |
| 4-Hydroxyestrone | <0.001 |
| Estrone | <0.001 |
| Estradiol | <0.001 |
| Estriol | 0.033 |
| 16-Epiestriol | <0.001 |
| Testosterone | <0.001 |
| Androsterone | <0.001 |
| Dehydroepiandrosterone | <0.001 |
| Cholesterol | <0.001 |
| Progesterone | <0.001 |
| Corticosterone | <0.001 |
| 4-Androsterone-3,17-dione | <0.001 |

From the above results, it is clear that the antibody of the invention is highly specific to estriol-3-sulfate, shows a little improvement in respect to cross-reactivity with other estrogen sulfates when immobilized on Sepharose 4B and exhibits no cross-reactions with other steroid conjugates and free steroids except dehydroepiandrosterone sulfate (0.77%), cholesterol sulfate (0.081%) and estriol (0.033%).

EXAMPLE 8

Figure 3:
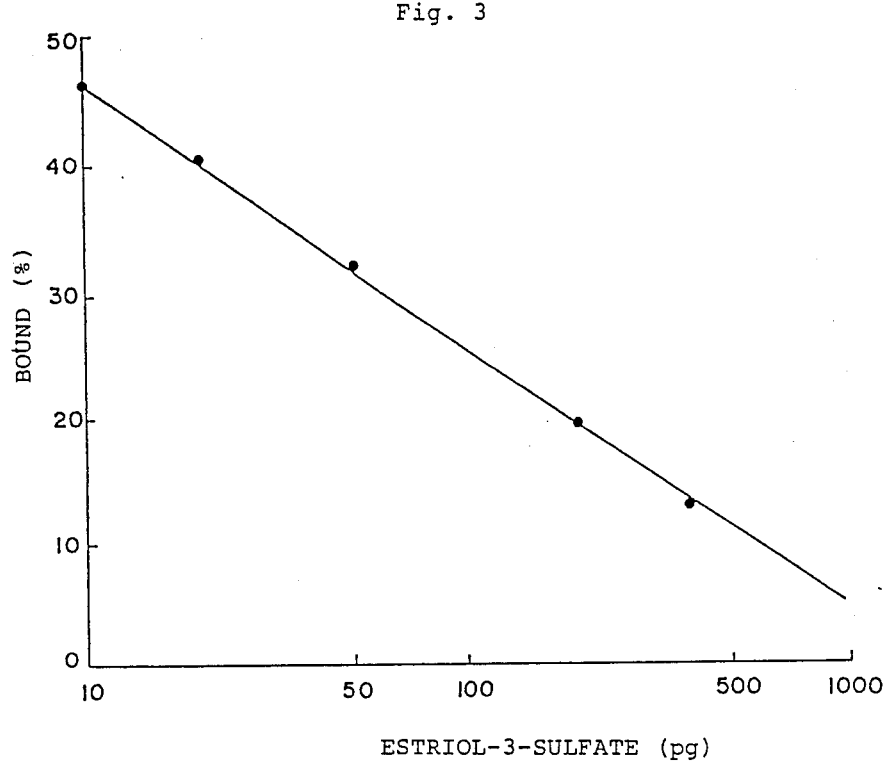

Accuracy test:

(A) Sensitivity. A calibration curve was constructed using a 1:500 dilution of the immobilized antibody by plotting the percent bound of labeled estriol-3-sulfate against various amounts of estriol-3-sulfate added to a diluted male plasma treated with a charcoal (cf. FIG. 3 of the accompanying drawings showing the calibration curve of estriol-3-sulfate to radioimmunoassay). The sensitivity was elucidated to be 15 pg, and estriol-3-sulfate can be determined in the range of 20 to 1000 pg.

(B) Recovery. A normal male plasma was treated with Norit A and diluted with water, and 0.1 ml aliquot of diluted plasma was added to the solution containing 0, 50, 100 and 400 pg of non-labeled estriol-3-sulfate. After incubation with a diluted immobilized antibody and the labeled compound, separation of the free and the bound steroid by centrifugation was carried out, and then the radioactivity was measured to determine the recovery percentage. Namely, the known amount of estriol-3-sulfate added to the normal male plasma was recovered and tested. The results are shown in Table 2, from which satisfaction was observed on the four levels.

TABLE 2

The accuracy of the assay by determination of estriol-3-sulfate added to male plasma

| Estriol-3-sulfate (pg/tube) | | | |
| --- | --- | --- | --- |
| Added | Expected | Found ± SD | CV (%)* |
| 0 | — | 29.7 ± 2.5 | 8.4 |
| 50 | 79.7 | 78.6 ± 3.4 | 4.3 |
| 100 | 129.7 | 126.7 ± 7.6 | 6.0 |
| 400 | 429.7 | 440.1 ± 35 | 7.7 |

*n = 5

(C) Variation test. Estriol-3-sulfate in pregnancy serum specimens was measured by the procedure as described in Exmaple 5, and the intraassay and interassay variations were investigated. The results are shown in Table 3. The interassay variations in the radioimmunoassay were measured with three different samples at points on the calibration curves. The coefficient variation (CV) values were less than 8.3% at each point. The interassay variations were measured with analysis of three different samples. The CV values were found to be less than 8.1%.

TABLE 3

The intraassay and interassay variations of the radioimmonoassay of estriol-3-sulfate in pregnancy plasma

| | Intraassay | | Interassay | |
| --- | --- | --- | --- | --- |
| Subject No. | Found ± SD (ng/ml) | CV (%)* | Found ± SD (ng/ml) | CV (%)* |
| 1 | 9.6 ± 0.6 | 6.2 | 8.2 ± 0.3 | 3.4 |
| 2 | 16.7 ± 0.8 | 4.8 | 17.5 ± 1.4 | 8.1 |
| 3 | 59.3 ± 4.9 | 8.3 | 61.5 ± 3.7 | 6.2 |

*n = 5

From the above results, it is understood that the immunoassay of estriol-3-sulfate by this invention is highly accurate.

EXAMPLE 9

Clinical test:

Blood levels of estriol-3-sulfate and estriol in every pregnancy week were determined for pregnancy plasma specimens from 40 patients. Measurement of estriol-3-sulfate was effected in the manner as shown in Example 5, while measurement of estriol was carried out in the manner as shown below.

A diluted pregnancy plasma (0.2 ml) was extracted with ether (1.0 ml) and washed with water (0.1 ml). [$^3$H]-estriol (10000 dpm) was added thereto, and the organic layer was dried under nitrogen stream. To the sample was added a diluted antiserum (1:6000) (0.25 ml) with borate buffer (0.05 mol/liter; pH, 8.0) (containing BGG (0.5 g/liter) and BSA (0.6 g/liter)). The resulting solution was incubated at room temperature for 1 hour, combined with ammonium sulfate (500 g/liter; 0.25 ml) and allowed to stand at room temperature for 15 minutes. The incubation mixture was centrifuged at 3500 rpm for 10 minutes, and a 0.2 ml aliquot of the supernatant was subjected to measurement.

Figure 4:
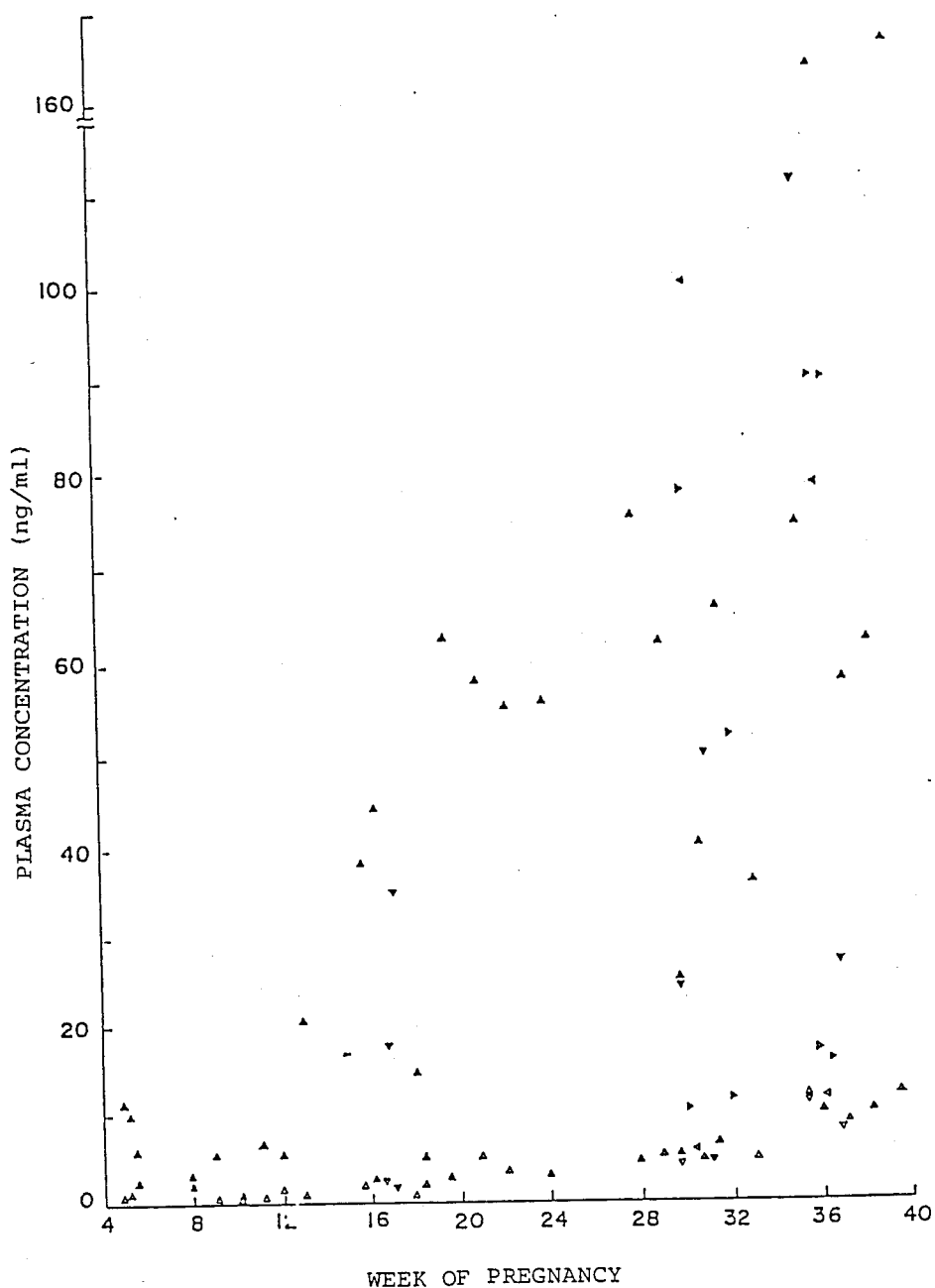

The results are shown in FIG. 4 of the accompanying drawing. This figure shows the plasma levels of estriol-3-sulfate and estriol in the normal pregnancy period,

What is claimed is:

1. A 6-substituted-estriol-3-sulfate protein conjugate of the formula:

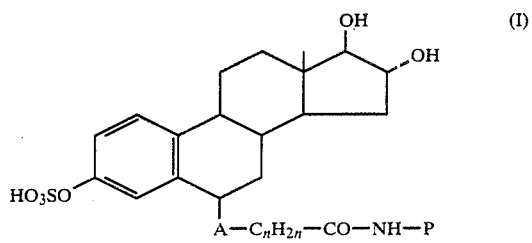

wherein A is =N—O— or —O—CO—, n is an integer of 1 to 4 and —NH—P is the residue of a protein excluding a hydrogen atom in the amino form therefrom.

2. The 6-substituted-estriol-3-sulfate protein conjugate according to claim 1, wherein A is =N—O—, n is an integer of 1 and —NH—P is the residue of albumin excluding a hydrogen atom in the amino form therefrom.

3. The 6-substituted-estriol-3-sulfate protein conjugate according to claim 2, wherein the albumin is bovine serum albumin.

4. The 6-substituted-estriol-3-sulfate protein conjugate according to claim 2, wherein the albumin is rabbit serum albumin.

5. The 6-substituted-estriol-3-sulfate protein conjugate according to claim 1, wherein A is =N—O—, n is an integer of 1 and —NH—P is the residue of globulin excluding a hydrogen atom in the amino form therefrom.

6. The 6-substituted-estriol-3-sulfate protein conjugate according to claim 5, wherein the globulin is bovine gamma globulin.

7. The 6-substituted-estriol-3-sulfate protein conjugate according to claim 1, wherein A is —OCO—, n is an integer of 2 and —NH—P is the residue of albumin excluding a hydrogen atom in the amino form therefrom.

8. The 6-substituted-estriol-3-sulfate protein conjugate according to claim 7, wherein the albumin is bovine serum albumin.

9. A reagent for producing an antibody having a specificity to estriol-3-sulfate which comprises a 6-substituted-estriol-3-sulfate pfotein conjugate in a sterilized liquid, said conjugate having the formula:

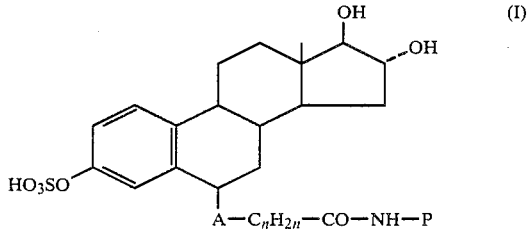

wherein A is =N—O— or —O—CO—, n is an integer of 1 to 4 and —NH—P is the residue of a protein excluding a hydrogen atom in the amino form therefrom.

10. The reagent according to claim 9, wherein A is =N—O—, n is an integer of 1 and —NH—P is the residue of albumin excluding a hydrogen atom in the amino form therefrom.

11. The reagent according to claim 10, wherein the albumin is bovine serum albumin.

12. The reagent according to claim 10, wherein the albumin is rabbit serum albumin.

13. The reagent according to claim 9, wherein A is =N—O—, n is an integer of 1 and —NH—P is the residue of globulin excluding a hydrogen atom in the amino form therefrom.

14. The reagent according to claim 13, wherein the globulin is bovine gamma globulin.

15. The reagent according to claim 9, wherein A is —OCO—, n is an integer of 2 and —NH—P is the residue of albumin excluding a hydrogen atom in the amino form therefrom.

16. The reagent according to claim 15, wherein the albumin is bovine serum albumin.

17. A method for determining estriol-3-sulfate in a specimen comprising utilizing an antigen-antibody reaction, said antibody having a specificity to estriol-3-sulfate, said antibody being produced by the use of a 6-substituted-estriol-3-sulfate protein conjugate of the formula:

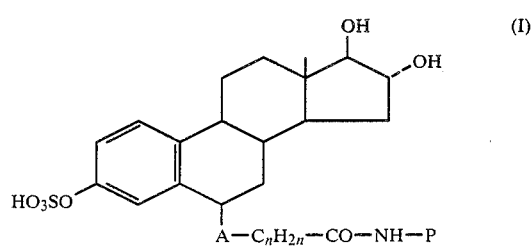

wherein A is =N—O— or O—CO—, n is an integer of 1 to 4 and —NH—P is the residue of a protein excluding a hydrogen atom in the amino form therefrom as an antigen.

18. The process according to claim 17, wherein the antigen-antibody reaction is effected in the presence of glutamine.

19. A kit for immunoassay of esteriol-3-sulfate in a specimen by utilization of an antigen-antibody reaction, which comprises (1) an antibody having a specificity to estriol-3-sulfate produced by the use of a 6-substituted-estriol-3-sulfate protein conjugate of the formula:

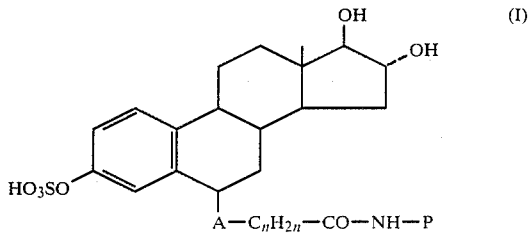

wherein A is =N—O— or —O—CO—, n is an integer of 1 to 4 and —NH—P is the residue of a protein excluding a hydrogen atom in the amino form therefrom as an antigen, and (2) labeled estriol-3-sulfate, respectively in separate containers.

* * * * *